(12) United States Patent
Pandya et al.

(10) Patent No.: US 12,718,930 B2
(45) Date of Patent: Aug. 25, 2026

(54) SELECTING TRAINING DATA FOR ANNOTATION

(71) Applicant: KONINKLIJKE PHILIPS N.V., Eindhoven (NL)

(72) Inventors: Maulik Yogeshbhai Pandya, Bangalore (IN); Anil Pawar, Bangalore (IN); Ravindra Patil, Bangalore (IN); Chaitanya Kulkarni, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 247 days.

(21) Appl. No.: 18/717,443

(22) PCT Filed: Nov. 17, 2022

(86) PCT No.: PCT/EP2022/082241
§ 371 (c)(1),
(2) Date: Jun. 7, 2024

(87) PCT Pub. No.: WO2023/104464
PCT Pub. Date: Jun. 15, 2023

(65) Prior Publication Data

US 2026/0162806 A1 Jun. 11, 2026

(30) Foreign Application Priority Data

Dec. 8, 2021 (EP) .................................... 21213178

(51) Int. Cl.
*G16H 30/40* (2018.01)
*G06T 5/40* (2006.01)
(Continued)

(52) U.S. Cl.
CPC ............... *G16H 30/40* (2018.01); *G06T 5/40* (2013.01); *G06T 7/0012* (2013.01); *G06T 7/13* (2017.01);
(Continued)

(58) Field of Classification Search
CPC ............................... G06T 7/0012–0016; G06T 2207/10064–10136;
(Continued)

(56) References Cited

U.S. PATENT DOCUMENTS

2013/0346346 A1 12/2013 Criminisi
2018/0232601 A1* 8/2018 Feng ..................... G06T 7/0004
(Continued)

OTHER PUBLICATIONS

Konyushkova, Ksenia, Raphael Sznitman, and Pascal Fua. "Introducing geometry in active learning for image segmentation." Proceedings of the IEEE international conference on computer vision. 2015. (Year: 2015).*
(Continued)

*Primary Examiner* — Atiba O Fitzpatrick

(57) ABSTRACT

A computer implemented method for use in selecting training data for annotation by an annotator as part of an active-learning machine learning process. The selected training data is for use in training a model to take as input a medical image and output a segmentation of the medical image. The method comprises: providing (202) an unlabeled medical image as input to the model and obtaining a segmentation of the unlabeled medical image as output from the model; a) determining (204) whether a geometric property of a segment of the segmentation satisfies a geometric criteria of a radiological feature represented by the segment; and/or b) determining whether an edge region of the segment satisfies an edge criteria. The method then comprises selecting (206) the unlabeled medical image as training data that is to be annotated by the annotator as part of the active-learning machine learning process, if the segment does not satisfy the geometric criteria and/or the edge criteria.

15 Claims, 6 Drawing Sheets

(51) Int. Cl.
*G06T 7/00* (2017.01)
*G06T 7/13* (2017.01)
*G06T 7/60* (2017.01)
*G06V 10/762* (2022.01)

(52) U.S. Cl.
CPC .............. *G06T 7/60* (2013.01); *G06V 10/762* (2022.01); *G06T 2207/30096* (2013.01)

(58) Field of Classification Search
CPC ... G06T 2207/30004–30104; G06T 7/10–194; G06T 2207/20021; G06T 2207/20112–20168; G06T 7/60; G06T 7/62; G06T 7/64; G06T 7/66; G06T 7/68; G06V 2201/03–034; G06V 10/25–273; G06V 20/49; G06V 20/695; G06V 40/162; G06V 20/80; G06V 20/698; G06N 3/091; A61B 5/7485; G06K 9/6224
See application file for complete search history.

(56) References Cited

U.S. PATENT DOCUMENTS

| | | | | |
|---|---|---|---|---|
| 2019/0065908 | A1* | 2/2019 | Lee | G06F 18/2155 |
| 2019/0325275 | A1* | 10/2019 | Lee | G06N 3/08 |
| 2021/0110147 | A1* | 4/2021 | Tsai | G06V 10/82 |
| 2021/0334955 | A1* | 10/2021 | Roth | G06T 7/0012 |
| 2022/0058369 | A1* | 2/2022 | Alahmari | G06F 18/285 |
| 2022/0138935 | A1* | 5/2022 | Hao | G06N 3/091 382/128 |
| 2022/0328189 | A1* | 10/2022 | Zhou | G06V 10/82 |
| 2022/0358658 | A1* | 11/2022 | Chaurasia | G06N 3/09 |
| 2022/0414428 | A1* | 12/2022 | Dube | G06N 3/084 |
| 2023/0147286 | A1* | 5/2023 | Hsiao | G06T 7/269 382/128 |
| 2025/0390744 | A1* | 12/2025 | Muffat | G06N 3/08 |

OTHER PUBLICATIONS

PCT International Search Report, International application No. PCT/EP2022/082241, Mar. 1, 2023.

Zhang et al., "Quality-Driven Deep Active Learning Method for 3D Brain MRI Segmentation", Neurocomputing, Elsevier, Amsterdam, NL, vol. 446, Mar. 20, 2021 (Mar. 20, 2021), pp. 106-117, XP086597462.

Top et al., "Active Learning for Interactive 3D Image Segmentation", Sep. 18, 2011 (Sep. 18, 2011), Advances in Biometrics : International Conference, ICB 2007, Seoul, Korea, Aug. 27-29, 2007; Proceedings; [Lecture Notes in Computer Science; Lect. Notes Computer], Springer, Berlin, Heidelberg, pp. 603-610, XP047463479.

Weicheng et al., "Cost-Sensitive Active Learning for Intracranial Hemorrhage Detection", arxiv.org, Cornell University Library, 201 Olin Library Cornell University Ithaca, NY 14853, Sep. 8, 2018 (Sep. 8, 2018), XP081188867.

Minaee S. et al., "Image Segmentation Using Deep Learning: A Survey", IEEE Transactions on Pattern Analysis and Machine Intelligence, vol. 44, No. 7, pp. 3523-3542, Jul. 1, 2022.

Badrinarayanan V. et al., "SegNet: A Deep Convolutional Encoder-Decoder Architecture for Robust Semantic Pixel-Wise Labelling", Computer Vision and Pattern Recognition (cs.CV), arXiv:1505.07293 [cs.CV], 2015.

Pedregosa et al., 'Scikit-Learn: Machine Learning in Python, Journal of Machine Learning Research, 12, pp. 2825-2830, 2011.

Burr S. et al., "Active Learning Literature Survey", University of Wisconsin Madison Department of Computer Sciences, 2009.

Dobrescu et al., "Diagnosis of Breast Cancer from Mammograms by Using Fractal Measures", International Journal of Medical Imaging, vol. 12, issue 2, 2013.

Budd S. et al., "A Survey on Active Learning and Human-in-the-Loop Deep Learning for Medical Image Analysis", Machine Learning (cs.LG); Computer Vision and Pattern Recognition (cs.CV); Human-Computer Interaction (cs.HC); Image and Video Processing (eess.IV), arXiv:1910.02923 [cs.LG], 2019.

Rajchl M. et al., "Employing Weak Annotations for Medical Image Analysis Problems", Computer Vision and Pattern Recognition (cs.CV), arXiv:1708.06297 [cs. CV], 2017.

Yoo D. et al., "Learning Loss for Active Learning", Computer Vision and Pattern Recognition (cs.CV); Machine Learning (cs.LG) arXiv:1905.03677 [cs.CV], 2019. https://arxiv.org/abs/1905.03677.

Kasarla T. et al., "Region-Based Active Learning for Efficient Labeling in Semantic Segmentation", 2019 IEEE Winter Conference on Applications of Computer Vision (WACV), Waikoloa, HI, USA, 2019, pp. 1109-1117. https://ieeexplore.ieee.org/document/8659293.

Vezhnevets A. et al., "Active Learning for Semantic Segmentation with expected Change", 2012 IEEE Conference on Computer Vision and Pattern Recognition, Providence, RI, USA, 2012, pp. 3162-3169. https://ieeexplore.ieee.org/document/6248050.

Hiasa et al., "Automated Muscle Segmentation from Clinical CT using Bayesian U-Net for Personalized Musculoskeletal Modeling", IEEE Transactions on Medical Imaging, (2019).

Jiang et al., "A Segmentation Method Based on Region Information and Edge Information", vol. J74-DII, No. 12, pp. 1651-1660, Dec. 1991.

* cited by examiner

SELECTING TRAINING DATA FOR ANNOTATION

FIELD OF THE INVENTION

The disclosure herein relates to machine learning, more particularly but non-exclusively, embodiments herein relate to selecting training data for annotation by an annotator as part of an active-learning machine learning process to train a model to segment a medical image.

BACKGROUND OF THE INVENTION

Segmentation of anatomy and lesions is an integral part of treatment planning for cancer and other similar diseases. Manual segmentation of anatomical features takes a long time and can only be performed by qualified expert radiologists. Therefore, various automated methods of segmentation have been developed, some of which use deep learning to segment medical images into different segments or portions corresponding to different features in the respective images. Due to recent advancements in the field of AI, machine learning (ML) models for segmentation have begun to exceed (individual) human performance. ML models for segmentation are described in the paper by S. Minaee, Y. Y. Boykov, F. Porikli, A. J. Plaza, N. Kehtarnavaz and D. Terzopoulos, "*Image Segmentation Using Deep Learning: A Survey*," in *IEEE Transactions on Pattern Analysis and Machine Intelligence*, doi: 10.1109/TPAMI.2021.3059968.

These tools work generally well on data similar to that on which the model has been trained, however with the ever-changing quality of the imaging and other image characteristics, models need to be frequently updated and re-trained as part of ongoing maintenance. Further training requires new annotated data e.g. new radiological images that are manually segmented in order to provide "ground truth" or correct annotations with which to train the model. Since obtaining the annotations for segmentation problems takes significantly more time and skill than classification problems involving simple descriptive labels, it can be difficult to obtain a large enough dataset with which to train an AI model to segment medical images.

It is thus an object of embodiments herein to reduce the annotation burden on expert human annotators when producing training data for segmentation models, without degrading the quality of the resulting models.

SUMMARY OF THE INVENTION

Active Learning/in-product learning is a supervised machine learning method whereby particular unlabeled data examples are strategically selected for annotation, and for use in further training of the model, according to which data examples are most likely to provide the most benefit (e.g. lead to the biggest improvement) to the training of the model. Active learning is a special case of supervised learning in which the active learning process itself is able to interactively query or request labels for data examples that are the most confusing or that the model is able to label with lowest confidence. For example, the model may select data examples for which the model has low confidence in its output, edge cases, or examples lying in a region of the input feature space that has previously been under-represented. In this way, the machine learning process prioritizes the annotation work i.e. instead of training data being provided in a more random manner, training data for annotation is selected strategically based on which data is most uncertain/complex and/or informative with which to seed the model. The selected training examples are then sent to an annotator for annotation and the model is then trained on the selected annotated data. The process is repeated until there is improvement in a scoring metric for the model. In this way, the model is only trained on the most important data, and full annotations only need to be provided on a selected subset of data examples, rather than the full dataset that would be required if the training data were selected in a traditional manner. By learning from the most informative cases first, active learning tends to lead to similar or generally better outcomes than traditional fully supervised methods.

Active Learning is often used for classification problems where it can be comparatively straight forward to select samples from an unlabeled pool of data examples that are confusing to the model. For example, in a classification problem, the output probability can be used as a criterion for selecting samples from an unlabeled pool of data, based on output probability values (e.g. by selecting data examples from the pool that the model classified with low confidence).

In the medical field, radiologists spend a lot of time segmenting (e.g. outlining structures in) images of lesions (such as tumors), organs at risk and organs for treatment planning. Deep-learning based segmentation models can assist radiologists to optimize their workflows. In theory, active learning provides an efficient mechanism with which to choose appropriate training data examples for labelling from a pool of unlabeled training examples, thus minimizing the annotation effort needed from radiologists whilst maximizing the improvement in the model for each annotation received. However, in practice, the criterion for selecting data examples from an unlabeled pool of samples is not as clearly defined for segmentation problems as it is for more simple classification problems, and is generally more complex.

Thus, it is an object of embodiments herein to provide improved methods of selecting unlabeled medical images for annotation and subsequent training of a model to segment medical images.

Thus, according to a first aspect, there is provided a computer implemented method for use in selecting training data for annotation by an annotator as part of an active-learning machine learning process to train a model to take as input a medical image and output a segmentation of the medical image. The method comprises: providing an unlabeled medical image as input to the model and obtaining a segmentation of the unlabeled medical image as output from the model; (a) determining whether a geometric property of a segment of the segmentation satisfies one or more geometric criteria of a radiological feature represented by the segment; and/or (b) determining whether an edge region of the segment satisfies one or more edge criteria; and selecting the unlabeled medical image as training data that is to be annotated by the annotator as part of the active-learning machine learning process, if the segment does not satisfy the one or more geometric criteria and/or the one or more edge criteria.

According to a second aspect there is a computer program product comprising a computer readable medium, the computer readable medium having computer readable code embodied therein, the computer readable code being configured such that, on execution by a suitable computer or processor, the computer or processor is caused to perform the method of the first aspect.

According to a third aspect there is a system for use in selecting training data for annotation by an annotator as part of an active-learning machine learning process to train a model to take as input a medical image and output a segmentation of the medical image. The system comprises a memory comprising instruction data representing a set of instructions, and a processor configured to communicate with the memory and to execute the set of instructions. The set of instructions, when executed by the processor, cause the processor to: provide an unlabeled medical image as input to the model and obtain a segmentation of the unlabeled medical image as output from the model. The processor is further caused to (a) determine whether a geometric property of a segment of the segmentation satisfies one or more geometric criteria of a radiological feature represented by the segment; and/or (b) determine whether an edge region of the segment satisfies one or more edge criteria. The processor is further caused to select the unlabeled medical image as training data that is to be annotated by the annotator as part of the active-learning machine learning process, if the segment does not satisfy the one or more geometric criteria and/or the one or more edge criteria.

These and other aspects will be apparent from and elucidated with reference to the embodiment(s) described hereinafter.

BRIEF DESCRIPTION OF THE DRAWINGS

Example embodiments will now be described, by way of example only, with reference to the following drawings, in which.

DETAILED DESCRIPTION OF EMBODIMENTS

As described above, it is an object of embodiments herein to provide more efficient training of machine learning models for use in segmenting medical images. This object is achieved herein, through the use of active learning and through improved methods of selecting unlabeled medical images from a pool of unlabeled medical images, for labelling by a human expert or Oracle. Through improved selection of unlabeled medical images for labelling, the systems and methods herein save time and resources of human experts, whilst providing models of the same or higher quality.

Figure 1:
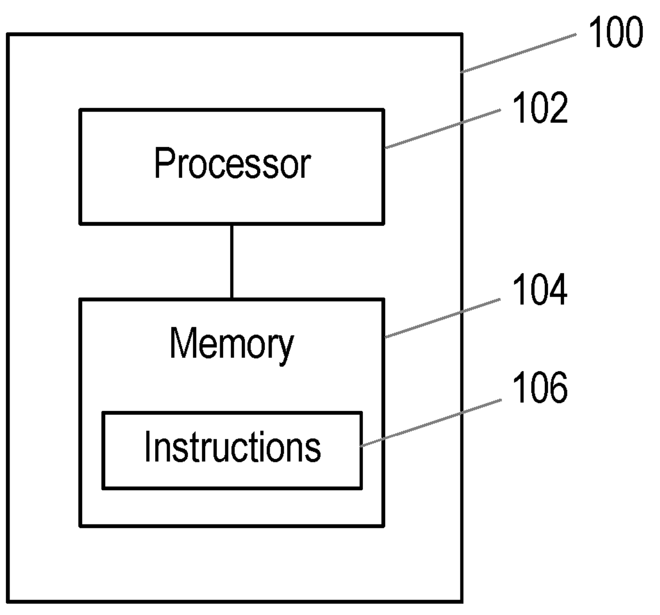
FIG. 1 is an apparatus according to some embodiments herein.

Turning now to FIG. 1 in some embodiments there is an apparatus 100 for use in selecting training data for annotation by an annotator as part of an active-learning machine learning process, according to some embodiments herein. Generally, the apparatus may form part of a computer apparatus or system e.g. such as a laptop, desktop computer or other computing device. In some embodiments, the apparatus 100 may form part of a distributed computing arrangement or the cloud.

The apparatus comprises a memory 104 comprising instruction data representing a set of instructions 106 and a processor 102 (e.g. processing circuitry or logic) configured to communicate with the memory and to execute the set of instructions. Generally, the set of instructions, when executed by the processor, may cause the processor to perform any of the embodiments of the method 200 as described below.

Embodiments of the apparatus 100 may be for use in selecting training data for annotation by an annotator as part of an active-learning machine learning process wherein the selected training data is for use in training a model to take as input a medical image and output a segmentation of the medical image. More specifically, the set of instructions, when executed by the processor, cause the processor to: provide an unlabeled medical image as input to the model and obtain a segmentation of the unlabeled medical image as output from the model. The processor is further caused to a) determine whether a geometric property of a segment of the segmentation satisfies a geometric criteria of a radiological feature represented by the segment; and/or b) determine whether an edge region of the segment satisfies an edge criteria; and select the unlabeled medical image as training data that is to be annotated by the annotator as part of the active-learning machine learning process, if the segment does not satisfy the geometric criteria and/or the edge criteria.

The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method described herein. The processor 102 can comprise one or more processors, processing units, multi-core processors and/or modules that are configured or programmed to control the apparatus 100 in the manner described herein. In some implementations, for example, the processor 102 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

The memory 104 is configured to store program code that can be executed by the processor 102 to perform the method described herein. Alternatively or in addition, one or more memories 104 may be external to (i.e. separate to or remote from) the apparatus 100. For example, one or more memories 104 may be part of another device. Memory 104 can be used to store the medical image, the segmentation, the model and/or any other information or data received, calculated or determined by the processor 102 of the apparatus 100 or from any interfaces, memories or devices that are external to the apparatus 100. The processor 102 may be configured to control the memory 104 to store the medical image, the segmentation, the model and/or the any other information.

In some embodiments, the memory 104 may comprise a plurality of sub-memories, each sub-memory being capable of storing a piece of instruction data. For example, at least one sub-memory may store instruction data representing at least one instruction of the set of instructions, while at least one other sub-memory may store instruction data representing at least one other instruction of the set of instructions.

It will be appreciated that FIG. 1 only shows the components required to illustrate this aspect of the disclosure and, in a practical implementation, the apparatus 100 may comprise additional components to those shown. For example, the apparatus 100 may further comprise a display. A display may comprise, for example, a computer screen, and/or a screen on a mobile phone or tablet. The apparatus may further comprise a user input device, such as a keyboard, mouse or other input device that enables a user to interact with the apparatus, for example, to provide initial input parameters to be used in the method described herein. The apparatus 100 may comprise a battery or other power supply for powering the apparatus 100 or means for connecting the apparatus 100 to a mains power supply.

The medical images referred to herein may be two-dimensional (2D) images or three-dimensional (3D) images. The medical images can be of any modality, such as computed tomography (CT) images, magnetic resonance (MR) images, ultrasound (US) images, X-ray images, positron emission tomography (PET) images, single photon emission computed tomography (SPECT) images, nuclear medicine images, or any other medical images.

The medical images herein may be made up of (e.g. comprise) image components which, as used herein, refer to the pixels in 2D images or the voxels of 3D images. The medical images herein may be in any suitable format, such as for example, the Digital Imaging and Communications in Medicine (DICOM) image format.

The model is for use in segmenting medical images. The skilled person will be familiar with segmentation (e.g. image segmentation), but in brief, segmentation involves extracting shape/form information about the objects or shapes captured in an image. This may be achieved by converting the image into constituent blocks or "segments", where the pixels or voxels assigned to each segment have a common attribute. For example, segmentation may involve outlining (creating contours of) the structures in the medical image, labelling image components according to the structure to which they correspond and/or adding color or texture to different structures in the medical image.

The systems and methods herein relate to Machine Learning (ML) segmentation whereby a ML model is used to convert an image into a plurality of constituent shapes (e.g. block shapes or block volumes), based on similar pixel/voxel values and image gradients. A recent review of the use of deep-learning in image segmentation is given in the paper by S. Minaee, Y. Y. Boykov, F. Porikli, A. J. Plaza, N. Kehtarnavaz and D. Terzopoulos, "*Image Segmentation Using Deep Learning: A Survey*," in *IEEE Transactions on Pattern Analysis and Machine Intelligence*, doi: 10.1109/TPAMI.2021.3059968.

The model may be any model trained using a machine learning process to take as input a medical image and output a segmentation of one or more structures in the medical image. For example, the model may be trained to segment an anatomical feature (e.g. part of the anatomy) or lesions (single or multiple) present in a particular anatomical feature. As an example, the model may be trained to segment the liver and/or lesions in the liver. This is merely an example however, and the model may be trained to segment other anatomical features and/or lesions in other anatomical features.

Examples of models that may be trained to perform image segmentation include but are not limited to convolutional neural networks, U-Nets and Encoder-decoder architectures (see paper on "SegNet" by Badrinarayanan et. al. (2015)). These are merely examples and the skilled person will appreciate that the disclosure herein applies equally to any type of model that can be trained to perform a segmentation task on medical images that can be trained using an active-learning process.

The model herein may have had initial training. For example, the model may have been trained on an initial training data set comprising training examples, each training example comprising i) an example medical image and ii) a segmentation of said example medical image. The segmentation for each training example may have been provided by a radiologist. As such, the segmentation for each training example represents the "ground truth" segmentation for that training example. The initial training data set may have been selected in any manner (e.g. randomly or based on the available annotated medical images etc). The model may have been initially trained on the initial training data set according to a supervised machine learning process (e.g. using techniques such as back propagation, gradient descent etc), in a known manner. For example, initial training may be performed using an opensource library such as Scikit-learn which is described in the paper: "Scikit-learn: Machine Learning in Python"; Pedregosa et al., JMLR 12, pp. 2825-2830, 2011.

Following the initial training, the model is subsequently trained using an active learning process. Such subsequent or further training may be performed e.g. in order to update or refine the model. Updating may be for the purposes of re-training or refinement of the model. Further training may be performed to enable the model to be able to segment a wider range of input images (e.g. to extend the model), to enable the model to keep up-to-date with changes to the input images (e.g. due to improved quality, different manufacturer of the imaging equipment etc, new demographic of patient data, use of the model at a different hospital), or for any other reason.

Generally, some initial training (as described above) is performed before active learning takes place, however it will be appreciated that active learning could equally be used directly on a new model (e.g. with random weights and/or biases).

The skilled person will be familiar with active learning, otherwise known as query learning or in-product learning. Assuming that there is a huge amount of unlabeled data available free of cost, active learning leverages the help of the model to determine which unlabeled data needs to be labelled and fed to the model for retraining. E.g. which examples from a pool of unlabeled data samples should be labelled and used as training data in order to best improve the model. In this way, training data can be labelled selectively, better utilizing the expertise and limited resources of the (human) labeller. Active Learning techniques are reviewed in the paper by Settles, Burr (2009) entitled, "Active Learning Literature Survey", that is published by the University of Wisconsin-Madison Department of Computer Sciences.

As used herein, the human expert may be referred to as the labeller, "Oracle" or annotator of the selected unlabeled data examples in the Active Learning process. The annotator is any expert qualified to segment the data. E.g. generally a radiographer who is able to provide a correct ("ground truth") segmentation for the selected training data from the pool of unlabeled data samples.

Figure 2:
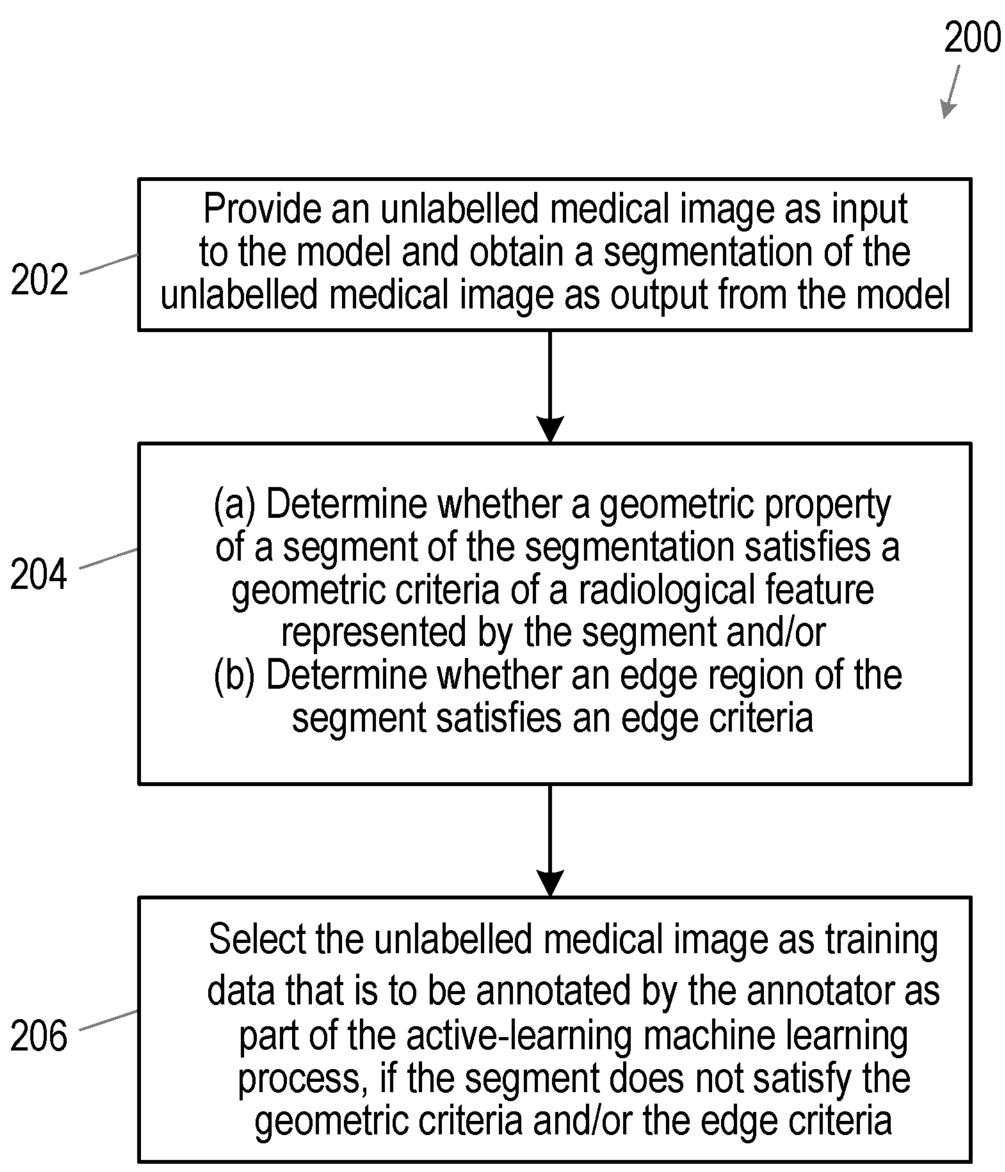
FIG. 2 is a method according to some embodiments herein.

Turning to FIG. 2, there is a computer implemented method 200 for use in selecting training data for annotation by an annotator as part of an active-learning machine learning process, wherein the selected training data is for use in training a model to take as input a medical image and output a segmentation of the medical image. For example, the model may output a segmentation of an anatomical feature and/or lesion in the medical image. Embodiments of the method 200 may be performed, for example by an apparatus such as the apparatus 100 described above.

Briefly, in a first step 202, the method 200 comprises: providing an unlabeled medical image as input to the model and obtaining a segmentation of the unlabeled medical image as output from the model. In step 204 the method comprises: a) determining whether a geometric property of a segment of the segmentation satisfies a geometric criteria of a radiological feature represented by the segment; and/or determining whether an edge region of the segment satisfies an edge criteria. In step 206 the method comprises: selecting the unlabeled medical image as training data that is to be annotated by the annotator as part of the active-learning machine learning process, if the segment does not satisfy the geometric criteria and/or the edge criteria.

The unlabeled medical image may be retrieved from a pool of unlabeled medical images, e.g. from a hospital or hospital(s) or any other database of relevant data. For example, it may be retrieved from a picture archiving and communication system (PACS). "Unlabeled" in this sense means that it has not been sent for labelling to an oracle, e.g. radiologist in order to obtain a ground-truth segmentation.

The unlabeled medical image may have been selected from the pool of unlabeled medical images according to the input parameters of the model. E.g. it will have the same modality and be an image of the same anatomical feature(s) as that taken as input by the model. Furthermore, the subject (e.g. patient) in the image will satisfy any demographic constraints applicable to valid inputs to the model (e.g. the model may be trained to only take inputs for particular patient demographics).

In step 202, the unlabeled medical image is provided (or fed) as input to the model (in the normal way). The model processes the unlabeled medical image and provides a segmentation of the medical image as output.

In option a) of step 204, as noted above, it is determined whether a geometric property of a segment of the segmentation satisfies a geometric criteria of a radiological feature represented by the segment. In option b) (which may be performed alternatively or in addition to option a), it is determined whether an edge region of the segment satisfies an edge criteria. Thus, it is automatically identified through the use of a geometric criteria and/or an edge criteria whether the segment is likely to be correct, or incorrect. If the segment is likely to be incorrect, then the unlabeled image is selected for annotation by an annotator (radiologist) in step 206, so that this image along with its annotation (which is taken as ground truth) can be used as training data to train the model.

As noted above, the model outputs a segmentation of the unlabeled medical image. The segmentation comprises a segment (which may otherwise be known as a mask) corresponding to a particular radiological feature in the unlabeled medical image.

The radiological feature may be an anatomical feature (e.g. organ, liver, heart, part of the vascular structure, or any other anatomical feature), a lesion (e.g. tumor) or any other feature imaged in the unlabeled medical image.

The geometric criteria may be a criteria associated with the particular shape of the radiological feature to which the segment corresponds. For example, if the segment corresponds to a lesion, then the geometric criteria may relate to typical (or expected) geometric shapes associated with lesions. If the segment corresponds to an anatomical feature, then the geometric criteria may relate to typical (or expected) geometric shapes associated with the particular anatomical feature.

As described in more detail below, the geometric feature may be related to the fractal dimension of the surface of the segment, the sphericity, or any other shape feature associated with the radiological feature to which the segment corresponds.

Generally, lesions of different organs have different geometric structures and limitations. For example, liver lesions are generally spherical in shape. Thus, the inventors herein have appreciated that geometry-based estimations can be used to select informative cases for annotation in an active learning framework.

In some embodiments, where the unlabeled medical image comprises an image of a lesion (e.g. tumor or cancer), a segment representing the lesion can be verified (e.g. as likely to correspond to a real tumor) according to the fractal dimension (FD) of its surface. Generally, FD increases with complexity and roughness of a structure. Particularly for cancer, it has been proven that FD increases with aggressiveness. See paper entitled: "*Diagnosis of Breast Cancer from Mammograms by Using Fractal Measures*" by Dobrescu (2013). Malignant tumors generally have higher FD because they are more ragged and spiculated than benign masses. So, if a lower FD is obtained from a segment for a predicted lesion, it indicates that either the lesion is benign or the model has performed under segmentation. Either way, the unlabeled medical image may be selected and provided to the annotator, for annotation to improve model performance. So, a threshold fractal dimension can be put on the FD of a segment of a predicted lesion structure. If the FD is less than the threshold fractal dimension, then it is more likely not a cancer region and thus it is an incorrect segmentation of the unlabeled medical image that should be selected in step 206 in order to reduce false positives. The value of the threshold fractal dimension will change dependent on the segmentation task. For example, it may be set according to the anatomy and kind of lesion that is to be detected. An appropriate value may thus be set by subject matter experts, e.g. human engineers. The appropriate value of the threshold fractal dimension may also be set dependent on the training requirements of the model, for example a wider range of fractal dimension values might be selected in more training examples are needed.

Fractal dimensions for complex structures like lesions can be calculated in many ways. As an example, a box counting method may be used. In a box counting method, the surface is covered with small grids. To calculate the fractal dimension, it is determined how the count of grids covering the lesion changes as we change the grid size. If $N(\varepsilon)$ boxes are required to cover surface contour, S with grids of side length $\varepsilon$, the Fractal dimension (D) of contour S can be calculated as:

$$D = \lim_{\varepsilon \to 0} \frac{\log N(\varepsilon)}{\log(1/\varepsilon)}$$

In other words, in some embodiments of the method 200, the segment represents a lesion. In some embodiments, the lesion is a tumor. As noted above, a lesion is an abnormal region such as a cut, injury, infected region or a tumor. For example, the model may label a segment of the segmentation as a lesion. In such embodiments, the geometric property is a fractal dimension of the surface of the segment, and the geometric criteria is based on fractal dimensions observed on the surfaces of (real) lesions. For example, the step of determining 204 whether a geometric property of a segment of the segmentation satisfies a geometric criteria of a radiological feature represented by the segment may comprise determining the fractal dimension of the surface of the segment, comparing the determined fractal dimension to a threshold fractal dimension, and selecting the unlabeled medical image as training data if the determined fractal dimension is less than the threshold fractal dimension.

An appropriate threshold fractal dimension may be determined empirically, e.g. from the fractal dimensions of real lesions. The threshold fractal dimension may be based on an average (e.g. mode, mean, or median) fractal dimension observed in lesions. The threshold fractal dimension may be set according to the number of samples that are required for annotation and further training of the model (e.g. a higher threshold will result in fewer selections in step 206 than a lower threshold). It will be appreciated that this applies to embodiments where the medical image is 2D or 3D.

In this way, segments of lesions can be verified as correctly corresponding to a real lesion, or as corresponding to a false positive, based on the fractal dimension of the surface of the segment.

In other embodiments, a segment of a lesion can also be verified and/or determined as being a false-positive based on its sphericity in a 3D image (or its roundness in a 2D image). Sphericity values range between 0 and 1. It is expected that, as lesions don't grow in a specific direction, they will tend to have higher sphericity values. Thus, in some embodiments, unlabeled medical images for which the model has output a segment of a lesion with a sphericity below a threshold sphericity, can be selected in step 206 for annotation by an annotator according to the active learning method.

The sphericity coefficient, S can be calculated as:

$$S = \frac{\sqrt[3]{36\pi V_{segment}^2}}{A_{segment}}$$

where $V_{segment}$ is the volume of the segment and $A_{segment}$ is the area of the segment.

Put another way, in some embodiments, the segment represents a lesion, the geometric property is based on the sphericity of the segment, and the geometric criteria is based on sphericities observed in (real) lesions. For example, the step of determining 204 whether a geometric property of a segment of the segmentation satisfies a geometric criteria of a radiological feature represented by the segment may comprise determining a measure of sphericity of the segment, such as the measure S above, comparing the determined measure of sphericity to a threshold sphericity, and selecting the unlabeled medical image as training data if the determined measure of sphericity is less than the threshold sphericity.

An appropriate threshold sphericity may be determined empirically, e.g. from the sphericities of real lesions. The threshold sphericity may be based on an average (e.g. mode, mean, or median) sphericity observed in lesions. Furthermore, the threshold sphericity may be set according to the number of samples that are required for annotation and further training of the model (e.g. a higher threshold will result in fewer selections in step 206 than a lower threshold).

It will be appreciated that the sphericity is only an example and any other measure that can be related to sphericity may equally be used. For example, a measure of how extended the lesion is could equally be used. For example, a ratio of the minor to major axes. The criteria in such an example being that lesions that have a major axis (minor/major<threshold) are likely to be incorrectly labelled and should thus be sent for annotation in step 206.

In this way, segments of lesions can be verified as correctly corresponding to a real lesion, or as corresponding to a false positive, based on the sphericity of the segment.

Turning now to other embodiments, in some embodiments, an atlas of shapes is used to determine whether the segment is consistent with the radiological feature. For example, if a segment corresponds to the liver of a subject, then the segment may be compared to an atlas of liver shapes.

Put another way, in some embodiments, the step of: determining 204 whether a geometric property of a segment of the segmentation satisfies a geometric criteria of a radiological feature represented by the segment comprises fitting shapes from an atlas of shapes of the radiological feature to the segment and selecting the unlabeled medical image as training data if the overlap between the best fitting shape from the atlas of shapes is less than a threshold overlap.

The threshold overlap may vary dependent on the particular training requirements of the model and/or the number of training examples required. For example, the threshold overlap may be increased if too many unlabeled medical images are flagged for annotation, or alternatively lowered if more unlabeled images are needed.

In more detail, imaging of a human body usually involves segmenting an organ within a body and most organs tend to have similar shapes. Badly mis-segmented samples can be identified by mapping the atlas on to every segmentation output. Atlas mapping is performed by registering the atlas on to the mask/segment. The registration method used can be deformable to get a better estimate. One way of measuring the quality of the segmented output is using the following formula:

$$\text{Overlap Coefficient} = \frac{(\text{Atlas Area}) \cap (\text{Segmented Area})}{(\text{Atlas Area})}$$

The above equation helps compute the amount of overlap (Overlap Coefficient), the intersection of the atlas area and segmented area is taken then divided by the atlas area. This gives a good estimate if there is a lot of under segmentation observed following registration.

$$\text{Exclusivity Coefficient} = \frac{\text{Segmented Area} - [(\text{Atlas Area}) \cap (\text{Segmented Area})]}{(\text{Segmented Area})}$$

The Exclusivity Coefficient may also be calculated, this provides information on how much of the segmentation from the model is different from the atlas. The weighted summation of the Overlap coefficient and the Exclusivity Coefficient can be used to provide an Atlas Coefficient as follows:

$$\text{Atlas Coefficient} = \frac{w1 * \text{Overlap Coefficient} + w2 * \text{Exclusivity Coefficient}}{w1 + w2}$$

w1 and w2 are weights, the values of which can be set or changed depending on the problem. The Atlas Coefficient works very well for segmentation problems where the shape of the segmentation is already known, such as organ segmentation. In cases such as lesion segmentation, this technique can be used to verify if the lesion falls in the correct organ. This can be used for detecting false positive lesions and also used to check if the lesion segmentation falls within or outside of an organ.

Thus, in embodiments where the radiological feature is a lesion or tumor, associated with an organ, the method 200 may comprise fitting shapes from an atlas of shapes to a second segment (in the segmentation) representing the organ. The best fitting shape from the atlas may then be used to determine which organ the lesion is associated with or forms part of. The relative locations of the lesion and organ may be established. Furthermore, false-positive labels of lesions associated with particular organs may be identified if a segment corresponding to the lesion is found not to be co-located with another segment corresponding to said particular organ. Co-located in this sense may mean that the segments overlap, at least partially.

Generally, to compute the atlas coefficient described above, an appropriate atlas needs to be selected. The altas selection process depends on patient demographic information such as Age, gender, race and country of origin. For a particular age group of a particular gender, the atlas may be selected to make the atlas coefficient more "context aware" and accurate. There may also be separate atlases for each country or place, as it has been observed that there are vast physiological changes across patients of various race and in different countries.

A "context aware" rule engine may be used to link patient specific metadata with performance of model. Here, patient specific information may be extracted such as gender, age group, geographical location, and/or organ in order to create an organ specific atlas. Variation from such atlas to the predicted segment of the model (as output by the model) can be computed using a distance matrix. The distance matrix (such as the KL divergence) may be used to select or reject the image for active learning.

Figure 4:
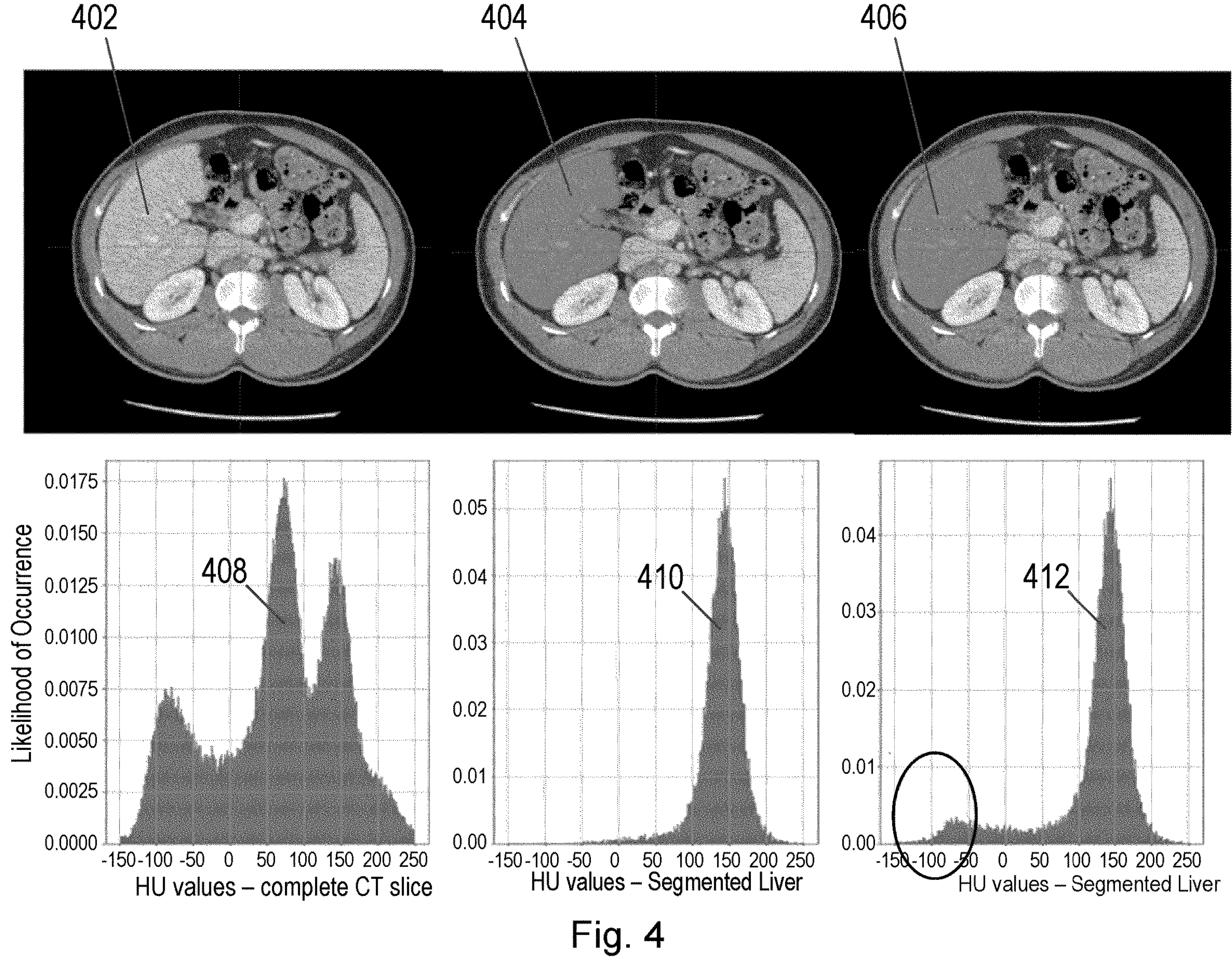
FIG. 4 shows an example whereby volumetric information from an atlas of liver shapes is compared to volumetric information of a segment of the liver in order to determine over- or under-segmentation.

FIG. 4 (top left hand) shows an example CT slice through a liver 402. The middle image in FIG. 4 shows an accurate segmentation 404 of the liver, and the right hand image shows an inaccurate segmentation 406 of the liver. Histograms are also shown for the distribution of intensity values for the whole image slice 408, the accurate liver segmentation 410 and the inaccurate liver segmentation 412.

From the segmented regions, statistical features such as Radiomics as well as histogram-based features may be extracted. For example, in the case of a CT scan, the performance of (i.e., liver or lung) segmentation model can be determined from the data distribution using histogram analysis as shown in FIG. 4. This allows determination of whether the model is not performing well. Organ specific Volumetric information helps to determine over or under segmentation behavior of a model. For example, in the example of FIG. 4, the circled region of the histogram corresponding to the inaccurate segmentation 406 of the liver, indicates over-segmentation whereby image components not consistent with the expected distribution liver are included, creating a second peak (as circled) in the distribution of the segment, that is not present in the histogram of the correct segment 410.

The Kullback-Leibler (KL) divergence, $D_{KL}$, allows computation/quantification of the divergence between two distributions. The KL divergence can be used to quantify the divergence between a Histogram of the expected liver segmentation, "Q", e.g. from atlas, from a Histogram of the predicted liver segmentation, as output from the model, "P" as given in the equation below.

$$D_{KL}(P\|Q) = \sum_{x \in X} P(x) \log\left(\frac{P(x)}{Q(x)}\right)$$

Also, the nth percentiles (e.g., $5^{th}$, $10^{th}$, $90^{th}$, $95^{th}$) may be calculated for the expected distribution (from the atlas) and compared with those of the distribution of the segment output from the model.

$$R = \frac{P \times (N+1)}{100}$$

$$\text{Percentile Value} = \begin{cases} S(R) & (\text{if } R \in Z) \\ (S(R_{I+1}) - S(R_I)) \times R_F + S(R_I) & (\text{else}) \end{cases}$$

Where, R is a rank, P is percentile and S is sorted array of N number of elements (items) in each histogram. $R_I$ and $R_F$ are integer and fractional part of R respectively.

As an example, for illustration purposes: Condition 1: Assume N=999 and p=10 This gives R=100, and thus the 100th element is selected from sorted array S. Condition 2: Assume N=100 and p=10 This gives R=10.1, so, integer part R_I=10 and fractional part R_F=0.1.

In this way, volumetric information of the segment and atlases may also be compared. As such, the method 200 may comprise in step 204, matching the radiological feature to an atlas of shapes of the radiological feature, according to demographic characteristics of the subject of the medical image. The method may then comprise obtaining expected volumetric information for the radiological feature from the matched shape from the atlas of shapes. CT and MR scans are generally 3D scans, and volumetric information in this sense means any information (features) extracted across such 3D scans. The expected volumetric information for the radiological feature may then be compared to volumetric information of the segment, e.g. using measures such as $D_{KL}$ and the percentiles described above, in order to determine whether there is under-segmentation or over-segmentation of the segment compared to the expected volumetric information for the radiological feature. For example, a histogram of the expected volumetric information from the atlas may be compared to a histogram of the volumetric information of the segment.

Turning now to other embodiments, in step 204, alternatively or additionally to the geometric-based criteria herein, an edge criteria may be used to determine whether an edge region of the segment satisfies an edge criteria. The edge criteria may be a criteria defining well-defined edges of a segment. Thus, edges or edge regions may further be used to determine whether a segment is likely to be over- or under segmented and thus whether the unlabeled medical image should be sent for annotation in step 206.

An edge region may be any region encompassing part of the edge of the segment. In some examples, an edge region may follow the outline of the surface of the segment, e.g. the edge region may be a band encompassing the edge region and following the outline of the edge region (e.g. with outer and inner surfaces parallel to the surface of the segment). An edge region may alternatively be defined relative to the center of gravity, or centroid of the segment, for example, e.g an edge region may be bounded by two concentric spherical surfaces centered on the centroid of the segment.

In some embodiments, the edge criteria is a threshold gradient between values of image components (e.g. pixels or voxels) within the segment and values of adjacent image components outside the segment, in order for the segment to be classed as having a well-defined edge.

As an example, if the sum of gradients in the original image along the edge/surface of each segment (in other words at the predicted mask contour), is less than a threshold gradient, then the segment can be labelled as being an uncertain segmentation, which should be sent for annotation in step 206. For example, a gradient coefficient, G, can be calculated for a contour outlining the segment. Nx, Ny Nz are co-ordinates of the set of points on the periphery of the predicted contour/segment S. dl is the derivation of the segmented volume in the x, y and z directions and $\nabla_{(x,y,z)}$ is gradient value, e.g. the change of Intensity at each point on the periphery of the segment:

$$\nabla_{x,y,z} = \sqrt{\left(\frac{dI}{dx}\right)^2 + \left(\frac{dI}{dy}\right)^2 + \left(\frac{dI}{dz}\right)^2}$$

$$G = N \Big/ \sum_{\substack{x \in N_x \\ y \in N_y \\ z \in N_z}} \nabla_{x,y,z}$$

G may then be compared to a threshold G value in step 204. A threshold value of the gradient coefficient, G value may be set according to the requirements of the training. Generally, lower G values indicate that the predicted segmentation is closer to the expected segmentation, and higher G values indicate the model is failing to predict the expected segmentation. Samples are therefore selected for active learning, if they are greater than a threshold G value. The value of G may be set by a human engineer, Higher values of G would result in fewer unlabeled images being selected compared to lower values of G; thus lowering the threshold, will increase the number of unlabeled medical images for annotation.

Turning now other embodiments, the edge criteria may be a criteria based on statistical features of clusters of image components in a border region (otherwise referred to herein as a penumbra region) encompassing the outer edge of the segment.

A border region may be defined in relation to the centroid or center of mass of the segment. For example, the center of mass of the segment may be determined. Then an outer surface of the border region may be defined, as a spherical surface centered on the center of mass and lying beyond the outer edge of the segment. An inner surface of the border region may be defined as a spherical surface centered on the center of mass and lying closer to the center of mass than the outer edge of the segment. The border region may then be defined as the volume between the outer surface and the inner surface.

The outer surface, may for example, be 30 percent further out than the outer edge of the segment and the inner surface may be 30 percent closer in than the outer edge of the segment. This is merely an example, however and the outer and inner surfaces may be at other distances, depending on factors such as the shape of the segment and/or the number of images required for the training.

The image components (voxels/pixels) may be clustered according to their values in the border region, e.g. using known clustering techniques. Each cluster may then be compared to the values at, or near to a central region of the segment to determine whether the cluster should be added to the segment or not. A central region may, for example, be a sphere centered on the centroid of the segment. The central region may encompass the center of gravity of the segment. The central region is closer to the center of the segment than the border region. Generally, the central region does not overlap the border region. A central region may also be referred to as a core region of the segment.

Thus, the method 200 may further comprise steps of: clustering image components in the border region into clusters; comparing the features of each cluster to image components in a central region of the segment, and selecting (206) the unlabeled medical image as training data that is to be annotated by the annotator as part of the active-learning machine learning process, based on the comparison between the clusters and the central region.

In other words step 206 may comprise selecting the unlabeled medical image as training data if the values of clusters of image components in the border region are statistically similar (comparable with) to the values of clusters of image components in a central region of the segment. The edge criteria may thus be whether image components in the border region are statistically similar to those in the central region (and should thus be added to the segment).

For example, for each cluster, a comparison may be made between the values of the image components in the cluster and the values of image components in the central region. A comparison may be made between statistical properties of values of the image components in the cluster and corresponding statistical properties of the values of image components in the central region. The comparison may be made based on radiomics features of each cluster. For example, the (Euclidean) distance between feature values in the central region and feature values in the cluster; intensity variations in the cluster, which may be measured, e.g. via the mean squared error (MSE); entropy of the cluster and/or a likelihood measure of the cluster compared to the central region may be determined. A score for each cluster may be determined based on one or more of the radiomics measures described above. The scores for each cluster can be combined, e.g. as a summation or multiplication, so as to determine an overall score describing whether the clusters in the border region are likely to be over/under segmented regions. Thus, the score may be used as an indication of whether the segmentation is a good segmentation or a poor segmentation and thus, whether the unlabeled image should be sent for annotation in step 206.

Figure 3:
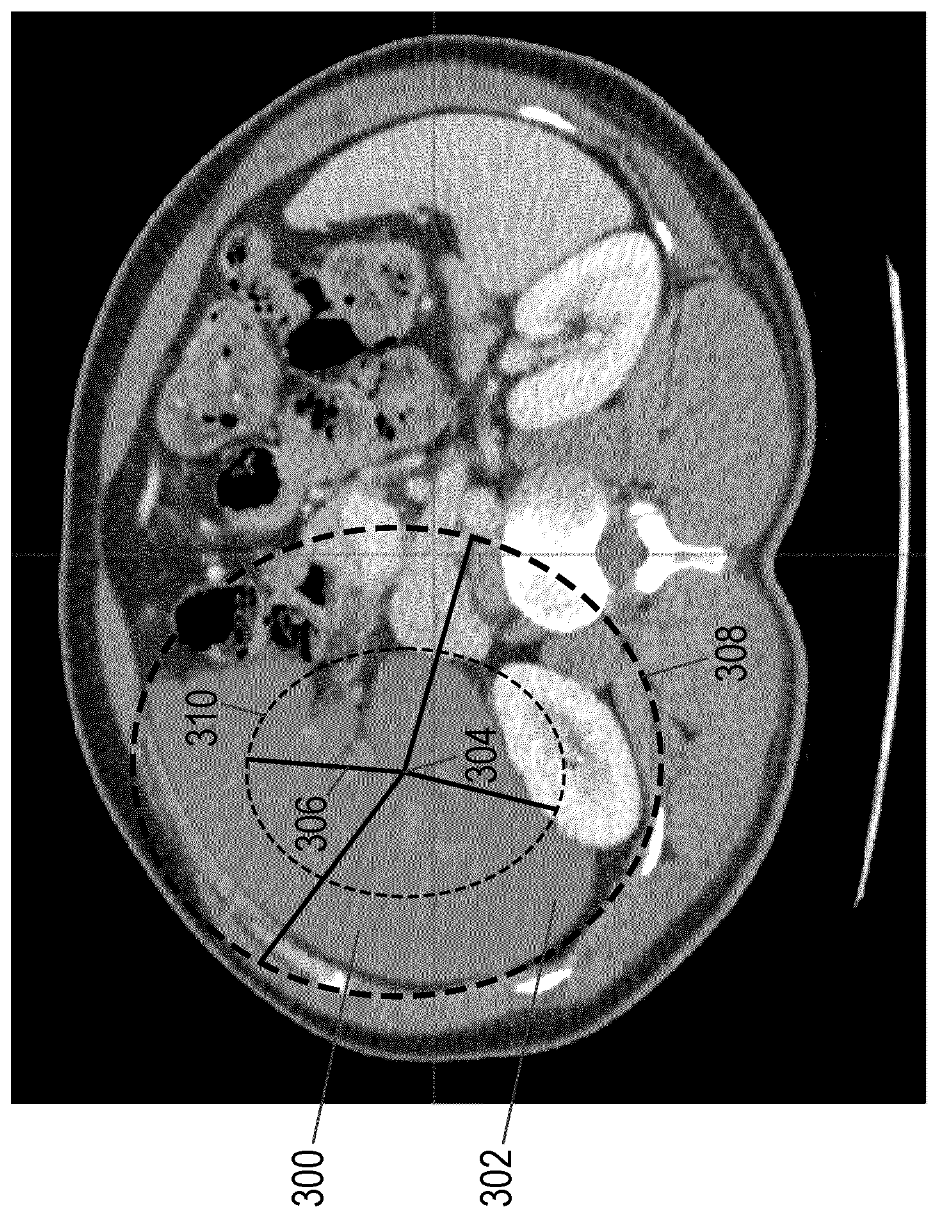
FIG. 3 shows an example where clusters of image components in a border region of a segment of a liver are compared to a central region of the segment in order to determine whether over- or under-segmentation has occurred.

This is described in more detail with respect to FIG. 3 which illustrates an example application of the method 200 to the segmentation of a 3D image of a liver 300 according to an embodiment herein. In this example, during the initial pass of the model, in step 202, all image component (e.g. pixel/voxel) values in the image are scored to assess whether the given image component is part of the liver or not. The liver in this example may be referred to as the “intended segment” or Region of Interest. In step 204, a border region 302 is defined as described above. A border region may be thought of as a “probability error zone”. The border region is determined according to the following steps:

Identify core 304 of the segment of the ROI (e.g. the center of gravity or centroid of the segment).

Identify the border region from the core of the ROI, by drawing perpendicular lines 306 from the core of the ROI outward radially.

The outer surface of the border region in FIG. 3 is defined as a surface 30% further out than the last identified image component in the ROI. E.g. 30% greater than the last segmentation boundary that is detected. This is illustrated as the thick dashed line 308 in FIG. 3.

Another inward circumference is created that is 30% less than the last segmentation boundary detected, this is used as the inner surface. This is illustrated as the thin dashed line 310 in FIG. 3.

The border region 302 is then the region between the outer and inner surfaces.

Heat map zones can then be created within the border region to ascertain the probability of pixel values that are close to decision boundary. Heat maps are created by analyzing the pixel intensity variation in the penumbra region (e.g. similar pixel intensities get similar heat values in the heat map).

The heat maps are further analyzed to assess if there is over or under segmentation quantitatively. The scoring function is derived based on the heatmap that helps to arrive at a score for the border region. As described above, the idea here is to compare extracted features within the core of the segment (where the segmentation is most certain) to the penumbra region (region of the segment with high uncertainty). This comparison is done using distance metrics (i.e., Euclidean distance) describing the "distance" between each feature.

Score Calculation:

Divide the border region into different clusters by clustering regions with similar attributes and compute a vector of radiomics features for each of the clusters. The vector of radiomics features may comprise, for example, measures such as the mean, variance and/or kurtosis of image components in the respective cluster.

Determine the Euclidean Distance (ED) between the vectors of radiomics features in each cluster and an (equivalent) vector of radiomics features measured in a central region of the segment, for each cluster. The intensity variations between the slices through mean squared error (MSE), entropy of a slice (ENT) and the likelihood measure (LLM) of an individual slice with respect to the normal/abnormal anatomy observed near the centroid of the segment can be computed. The measures can be computed as follow:

Euclidean Distance $$ED = \frac{1}{D}\sqrt{\sum_{i=1}^{D}\left(FV_C^i - FV_k^i\right)^2}$$

Where, $FV_C$ is the vector of radiomics features for the core region and $FV_k$ is the vector of radiomics features for the '$k$'$^{th}$ cluster in the border region (or super pixel from penumbra region, which is under question) and 'D' is the dimension of the vector of radiomics features. To validate, if a cluster belongs to the segmented region, the vector of radiomics features of the cluster should be similar to an equivalent vector of radiomics features in the central region. Similarity can thus be quantified using the ED.

Mean Squared Error $$MSE = \frac{1}{MN}\sum_{i=1}^{M}\sum_{j=1}^{N}[I_C(i,j) - I_k(i,j)]^2$$

Where, $I_C$ & $I_k$ are the intensity values of the central region and '$k$'$^{th}$ cluster. M and N correspond to the dimension of the respective ($k^{th}$) cluster in the image, e.g., an M×N cluster or image patch is considered for comparison with the central region.

$$\text{ENT} = -\Sigma_{O \subset \Omega} p_o(I)\ln(p_o(I)).$$

Where, $p_o(\bullet)$ is the probability density function for intensity value 'O' and 'Ω' is the set of all possible grey values in 'I'.

Log Likelihood Ratio $$\text{LLR} = \log[p(\text{FV}|S_A)] - \log[p(\text{FV}|S_N)]$$

Where, the '$S_N$', '$S_A$' are the Gaussian cluster models of segmented (within) and cluster under questions, cases derived from Step.1 and 'FV' is the feature vector.

The above described measures can be combined into a single score or probability that the cluster is part of the segment:

$$P(\text{Border Region}) = \text{Normalized}\left(\prod val(ED, MSE, ENT, LLR)\right)$$

Further, the value of P(Border Region) can be used as contributing factor to decide if the region is segmented correctly, or whether the image should be flagged for annotation in step 206. Higher values of P(Border Region) indicate good segmentation of the unlabeled medical image. To select cases where model is failing, a threshold value of P(Border Region) may be set. The method may comprise selecting unlabeled medical images for annotation that have a value of P(Border Region) below threshold value of P(Border Region).

Turning now to other embodiments, the skilled person will appreciate that a combination of the measures above may also be used. For example, a weighted combination of the Fractal Dimension, D, the gradient coefficient, G and the Sphericity, S as described above may be combined into a coefficient $G_s$ ("Geometry estimation coefficient"). For example, by taking a weighted sum:

$$G_S = w_1 D + w_2 G + w_3 S$$

A threshold value of the $G_s$ may be set. If a segment has a value of $G_s$ below this value, then the medical image may be sent for annotation in step 206.

The values of the weights $w_1$-$w_3$ can be set dependent on type of segmentation. For example, w3 may be set to a higher level for lesion segmentation compared to organ segmentation (as the sphericity is more relevant to lesion segmentation than organ segmentation). $w_2$ may be set to a higher level for organ segmentation, as sharp edges may be more important for organ segmentation compared to FD or Sphericity.

Another example score is given by the "retraining Confidence" measure:

$$\text{Retraining Confidence} = \frac{w1 * P(\text{Error Zone Score}) + w2 * \text{Atlas Coefficient} + w3 * G_S + w4 * D_{KL} + w5 * \text{Percentile Value}}{w1 + w2 + w3 + w4 + w5}$$

Again, this is a weighted combination of some of the estimations described above, whereby the weights are set based on the particular segmentation problem. For e.g. Lesions, the Atlas weights may be set very low (even to 0), whereas for organs the atlas weights may be set to larger values.

If the retraining confidence score is obtained for a plurality of unlabeled medical images (e.g. by repeating the method 200 on each), then the top n number of unlabeled medical images may be selected for re-training. The number n can be decided for example, based on the labeller's time availability and/or the cost of obtaining the ground truth annotations.

Turning back to the method 200, in step 206, the method comprises selecting the unlabeled medical image as training data that is to be annotated by the annotator as part of the active-learning machine learning process, if the segment does not satisfy the geometric criteria and/or the edge criteria.

For example, the unlabeled medical image may be selected as training data that is to be annotated and used as training data if the segment does not satisfy one or more of the criteria described above.

For example:

If the fractal dimension is less than the threshold fractal dimension.

If the sphericity is less than the threshold sphericity.

If the gradient of an edge region is less than the threshold gradient.

If the overlap between the best fitting shape from an atlas of shapes and the segment is less than a threshold overlap.

If the gradient in an edge region of the segment is less than a threshold gradient.

Then in step 206, the method comprises sending the unlabeled medical image to the annotator for annotation. The skilled person will appreciate that these are examples, and that other geometric and/or edge criteria may be defined that are different to those listed above or described elsewhere in this disclosure. Furthermore, combinations of the criteria above may also be used.

Following step 206, the selected unlabeled medical images are sent to the annotator (e.g. radiologist or other medical professional) in order to obtain a ground truth or "correct" segmentation for the unlabeled medical image. The medical image and the segmentation from the annotator are then used as training data with which to (re) train the model.

In embodiments where the probability error zone (border region) is determined, the annotator may be prompted to annotate only those regions containing clusters for which the system has low confidence, e.g. only in an error zone (they don't need to annotate completely, only a part of the mask has to be annotated and other part has to be verified). This is more efficient for the annotator.

The annotator checks and/or corrects mistake in the segmentation (or re-segments the unlabeled medical image entirely anew) and the resulting annotated medical image is added to the training data. The model can be retrained with both old training data and newly updated training data for better performance. The process of active learning can be performed on a timely basis, for eg. Once a week or once a month. This process helps keeps the model healthy in a product environment.

Figure 5:
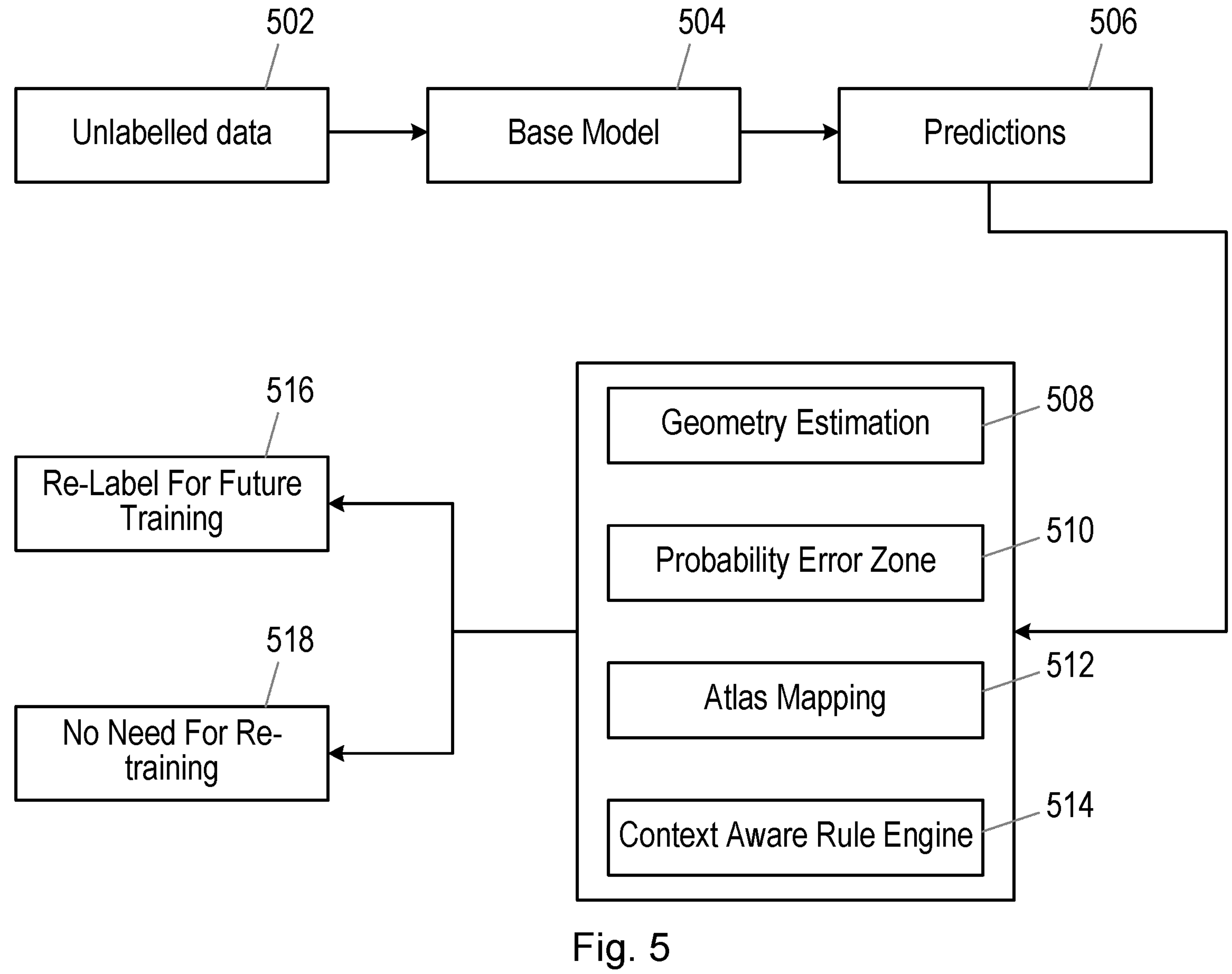
FIG. 5 shows an example method according to an embodiment herein.

This is illustrated in FIG. 5 which shows an example according to some embodiments herein. FIG. 5 illustrates an embodiment of the method 200 described above. The embodiment in FIG. 5 may be performed, for example, by the apparatus 100 described above.

In 502 an unlabeled medical image is selected and in 504 this is provided as input to a model. At 506, the model outputs (a prediction of) a segmentation of the unlabeled medical image. Steps 502, 504 and 506 are performed as part of step 202 of the method 200 as described above, and it will be appreciated that the detail therein applies equally to steps 502, 504 and 506.

A segment of the segmentation is then assessed by one or more of a geometry estimation module 508, a probability error zone module 510, an atlas mapping module 512 and a context aware rule engine module 514.

The geometry estimation module determines whether a geometric property of a segment of the segmentation satisfies a geometric criteria of a radiological feature represented by the segment. Various example geometric criteria were described in detail above (e.g. relating to sphericity, FD, etc) with respect to step 204 and the detail therein will be understood to apply equally to the Geometry Estimation module 508.

The probability error zone module 510 determines whether an edge region of the segment satisfies an edge criteria by comparing statistical features of clusters of image components in a border region encompassing the outer edge of the segment to those in a region close to the center of the segment, in order to determine over- or under-segmentation. This as described above with respect to FIG. 3 and step 204 of the method 200 and the detail therein will be understood to apply equally to the probability error zone module 510.

The atlas mapping module 512 fits shapes from an atlas of shapes of the anatomical feature to the segment and selects the unlabeled medical image as training data if the overlap between the best fitting shape from the atlas of shapes is less than a threshold overlap. The threshold overlap was described above with respect to step 204 and the detail therein will be understood to apply equally to the atlas mapping module 512.

The context aware rule engine 514 uses patient specific metadata with performance of model. Here, patient specific information may be extracted such as gender, age group, geographical location and/or organ in order to create a specific atlas. Variation from such atlas to the predicted segment of the model (as output by the model) may be used as a distance matrix, as described above with respect to step 204. The distance matrix was described above with respect to step 204 and the detail therein will be understood to apply equally to the context aware rule engine 514.

If the segment does not satisfy the geometric criteria and/or the edge criteria then the unlabeled medical data is selected for annotation by an annotator 516 and subsequently used in re-training the model. However, if the segment satisfies the aforementioned criteria then there is no need for annotation or re-training based on the unlabeled medical image and the method ends at 518.

In this way, there is a method and apparatus for selecting which unlabeled medical data should be send for annotation and used for further training of a model to segment medical images.

Figure 6:
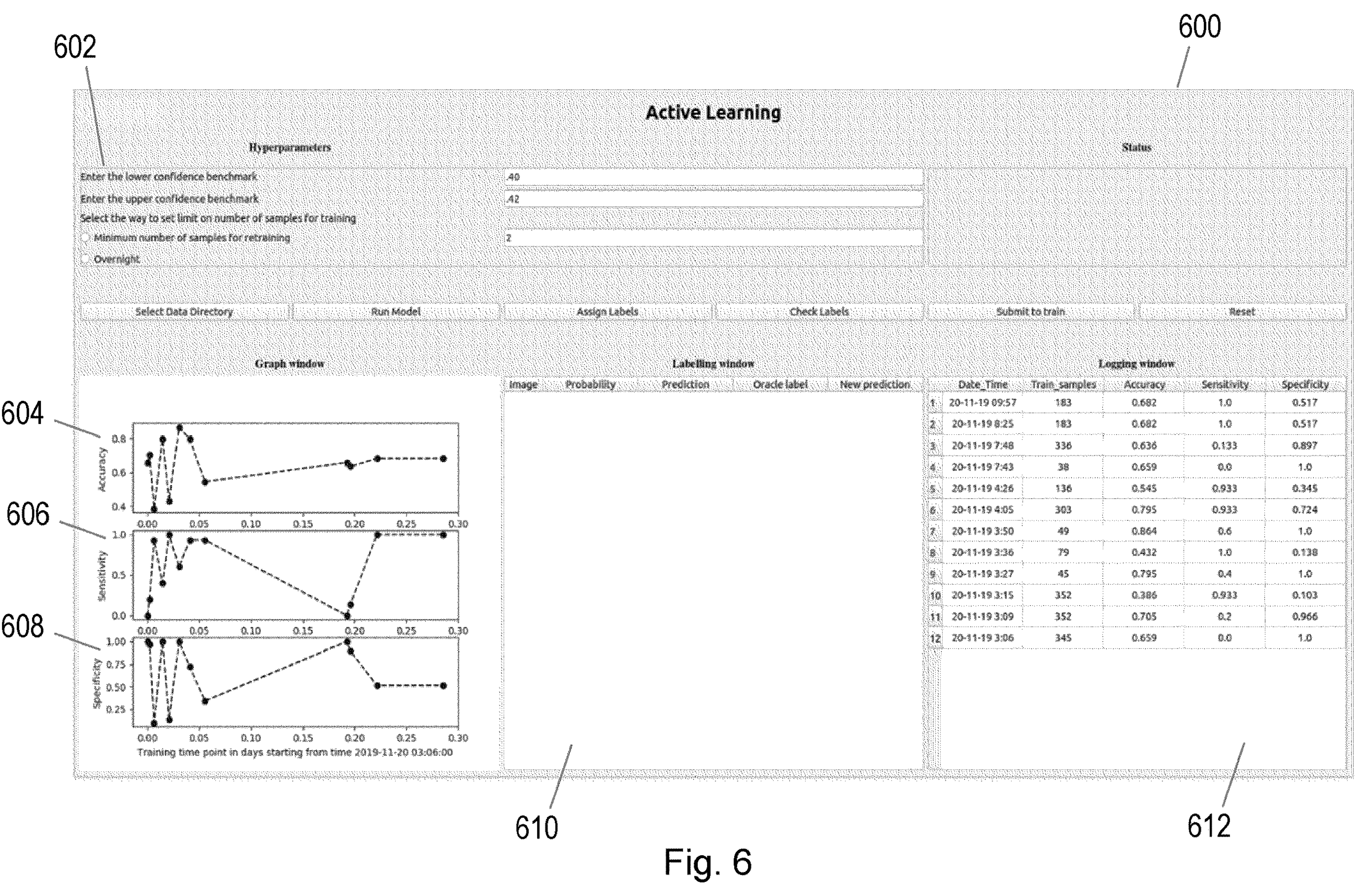
FIG. 6 shows an example GUI according to an embodiment herein.

FIG. 6 shows an example graphical user interface (GUI) that can be used to train a model according to the method 200 herein. The GUI 600 may be displayed on a display of the apparatus 100 described above. A user interface as shown in FIG. 6 can be built to perform active learning using the method 200. In this, a range of proposed retraining confidences/thresholds may be given 602, specifying the values for the thresholds described herein against which medical images should be assessed and be selected for annotation. A mode of retraining can also be given that specifies for example, a minimum number of selected samples above which retraining should be started, or when the training should be performed (e.g. it can be overnight training). In the example of FIG. 6, the GUI shows three windows, two for showing graphs 604, 606, 608 of metrics of model performance on the test set (which may be a validation set). An area 610 may be provided for displaying the selected unlabeled medical images for annotation (output in step 206 above). The dicom series may thus be openable in an inbuilt dicom viewer in 610. After annotation, retraining can be started using UI only and same steps will be repeated for further iterations of active learning. Window 610 may display various statistical properties of the unlabeled medical images.

Thus, a GUI as illustrated in FIG. 6 may be used to perform and customize the method 200 as described above.

In another embodiment, there is provided a computer program product comprising a computer readable medium, the computer readable medium having computer readable code embodied therein, the computer readable code being configured such that, on execution by a suitable computer or processor, the computer or processor is caused to perform the method or methods described herein.

Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer implemented method for use in selecting training data for annotation by an annotator as part of an active-learning machine learning process, wherein the selected training data is for use in training a model to take as input a medical image and output a segmentation of the medical image, the method comprising:

receiving an unlabeled medical image as input to the model and obtaining a segmentation of the unlabeled medical image as output from the model;

determining whether a geometric property of a segment of the segmentation satisfies one or more geometric criteria of a radiological feature represented by the segment; and/or determining whether an edge region of the segment satisfies one or more edge criteria; and selecting the unlabeled medical image as training data that is to be annotated by the annotator as part of the active-learning machine learning process, if the segment does not satisfy the one or more geometric criteria and/or the one or more edge criteria.

2. A method as in claim 1, wherein:

the segment represents a lesion;

the geometric property is a fractal dimension of the surface of the segment; and the one or more geometric criteria is based at least in part on fractal dimensions observed on the surfaces of lesions.

3. A method as in claim 2, wherein the step of determining whether a geometric property of a segment of the segmentation satisfies a geometric criteria of a radiological feature represented by the segment comprises:

determining the fractal dimension of the surface of the segment;

comparing the determined fractal dimension to a threshold fractal dimension; and selecting the unlabeled medical image as training data if the determined fractal dimension is less than the threshold fractal dimension.

4. A method as in claim 1 wherein:

the segment represents a lesion;

the geometric property is based at least in part on the sphericity of the segment; and wherein the one or more geometric criteria is based at least in part on sphericities observed in lesions.

5. A method as in claim 4, wherein the step of determining whether a geometric property of a segment of the segmentation satisfies one or more geometric criteria of a radiological feature represented by the segment comprises:

determining a measure of sphericity of the segment;

comparing the determined measure of sphericity to a threshold sphericity; and selecting the unlabeled medical image as training data if the determined measure of sphericity is less than the threshold sphericity.

6. A method as in claim 1, wherein the determining whether a geometric property of a segment of the segmentation satisfies one or more geometric criteria of a radiological feature represented by the segment comprises:

fitting shapes from an atlas of shapes of the radiological feature to the segment and selecting the unlabeled medical image as training data if the overlap between the best fitting shape from the atlas of shapes is less than a threshold overlap.

7. A method as in claim 1, wherein the radiological feature is a lesion in an organ and wherein the method comprises:

fitting shapes from an atlas of shapes to a second segment representing the organ; and using the best fitting shape from the atlas of shapes to determine:

the relative locations of the lesion and the organ; and/or whether the segment is a false-positive labelling of a lesion because the lesion is not co-located with the organ.

8. A method as in claim 1, wherein the step of: determining whether a geometric property of a segment of the segmentation satisfies one or more geometric criteria of a radiological feature represented by the segment comprises:

matching the radiological feature to an atlas of shapes of the radiological feature according to demographic characteristics of the subject of the medical image;

obtaining expected volumetric information for the radiological feature from the matched shape from the atlas of shapes; and comparing the expected volumetric information for the radiological feature to volumetric information of the segment to determine whether there is under-segmentation or over-segmentation of the segment compared to the expected volumetric information for the radiological feature.

9. A method as in claim 8, wherein the step of comparing the expected volumetric information for the radiological feature to volumetric information of the segment comprises: comparing a histogram of the expected volumetric information to a histogram of the volumetric information of the segment.

10. A method as in claim 1 wherein the one or more edge criteria is a threshold gradient between values of image components within the segment and values of adjacent image components outside the segment for the segment to be classed as having a well-defined edge.

11. A method as in claim 1, wherein the one or more edge criteria is based at least in part on statistical features of clusters of image components in a border region encompassing the outer edge of the segment.

12. A method as in claim 11, wherein the method comprises:

determining the center of mass of the segment;

defining an outer surface of the border region as a spherical surface centered on the center of mass and lying beyond the outer edge of the segment;

defining an inner surface of the border region as a spherical surface centered on the center of mass and lying closer to the center of mass than the outer edge of the segment; and determining the border region as the volume between the outer surface and the inner surface.

13. A method as in claim 12, further comprising:

clustering image components in the border region into clusters;

comparing the features of the clusters to image components in a central region of the segment; and selecting the unlabeled medical image as training data that is to be annotated by the annotator as part of the active-learning machine learning process, based at least in part on the comparison between the clusters and the central region.

14. A computer program product comprising a non-transitory computer readable medium, the computer readable medium having computer readable code embodied therein, the computer readable code being configured such that, on execution by a suitable computer or processor, the computer or processor is caused to perform the method as claimed in claim 1.

15. A system for use in selecting training data for annotation by an annotator as part of an active-learning machine learning process, wherein the selected training data is for use in training a model to take as input a medical image and output a segmentation of the medical image, the system comprising:

a memory comprising instruction data representing a set of instructions; and a processor configured to communicate with the memory and to execute the set of instructions, wherein the set of instructions, when executed by the processor, cause the processor to:

receive an unlabeled medical image as input to the model and obtain a segmentation of the unlabeled medical image as output from the model;

determine whether a geometric property of a segment of the segmentation satisfies one or more geometric criteria of a radiological feature represented by the segment; and/or determine whether an edge region of the segment satisfies one or more edge criteria; and select the unlabeled medical image as training data that is to be annotated by the annotator as part of the active-learning machine learning process, if the segment does not satisfy the one or more geometric criteria and/or the one or more edge criteria.

* * * * *